United States Patent
Mortimer

(10) Patent No.: US 11,117,000 B1
(45) Date of Patent: *Sep. 14, 2021

(54) METHOD OF CONTROLLING TRANSMISSION OF PARTICLES TO AND AWAY FROM A PERSON'S FRONTAL FACE REGION

(71) Applicant: John S. Mortimer, Frankfort, IL (US)

(72) Inventor: John S. Mortimer, Frankfort, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 17/101,635

(22) Filed: Nov. 23, 2020

Related U.S. Application Data

(63) Continuation-in-part of application No. 16/884,482, filed on May 27, 2020, now Pat. No. 11,027,157.

(Continued)

(51) Int. Cl.
| | |
|---|---|
| *A62B 23/02* | (2006.01) |
| *A62B 9/04* | (2006.01) |
| *A61F 9/02* | (2006.01) |
| *A62B 18/00* | (2006.01) |
| *A62B 18/08* | (2006.01) |
| *A41D 13/11* | (2006.01) |

(52) U.S. Cl.
CPC .......... *A62B 23/025* (2013.01); *A61F 9/029* (2013.01); *A62B 9/04* (2013.01); *A62B 18/00* (2013.01); *A62B 18/086* (2013.01); *A41D 13/1138* (2013.01); *A41D 13/1161* (2013.01)

(58) Field of Classification Search
CPC .... A62B 7/00; A62B 7/10; A62B 9/00; A62B 9/04; A62B 9/06; A62B 18/00; A62B 18/02; A62B 18/025; A62B 18/04; A62B 18/08; A62B 18/082; A62B 18/084; A62B 18/086; A62B 23/00; A62B 23/02; A62B 23/025; A62B 23/06; A41D 13/11; A41D 13/1107; A41D 13/1115; A41D 13/1123; A41D 13/113; A41D 13/1146; A41D 13/1153; A41D 13/1138; A41D 13/1161; A41D 13/1169; A41D 13/1176; A41D 13/1184; A61F 9/029; A61F 9/04; G02C 7/16; G02C 11/00; G02C 9/00; G02C 9/02; G02C 9/04; A42B 1/00181; A42B 1/247

See application file for complete search history.

(56) References Cited

U.S. PATENT DOCUMENTS

| | | | | |
|---|---|---|---|---|
| 2,758,307 A | * | 8/1956 | Treiber ................... | A61F 9/025 2/9 |
| 3,298,031 A | * | 1/1967 | Morgan ............. | A41D 13/1184 2/9 |

(Continued)

*Primary Examiner* — Colin W Stuart
(74) *Attorney, Agent, or Firm* — Wood, Phillips, Katz, Clark & Mortimer

(57) ABSTRACT

A method for a person to control transmission of particles to and away from his/her frontal face region including the step of obtaining a face covering apparatus with a frame that can be held on the person's head and a covering assembly on the frame. With the frame on the person's head, the wall structure on the covering assembly is movable between blocking and staging positions. In the former position, the wall structure blocks airborne particles moving toward and away from a person's nostrils and/or mouth. In the latter position, the wall structure does not reside directly forwardly of the person's frontal face region below a horizontal plane at or above a top of the person's mouth.

30 Claims, 12 Drawing Sheets

Related U.S. Application Data

(60) Provisional application No. 63/006,813, filed on Apr. 8, 2020.

(56) References Cited

U.S. PATENT DOCUMENTS

| | | | | |
|---|---|---|---|---|
| 3,768,100 | A * | 10/1973 | Colman | A41D 13/1161 |
| | | | | 2/9 |
| 4,805,639 | A * | 2/1989 | Dial | A41D 13/1153 |
| | | | | 128/857 |
| 5,647,060 | A * | 7/1997 | Lee | A41D 13/1184 |
| | | | | 2/9 |
| 5,956,760 | A * | 9/1999 | Wine | A42B 1/247 |
| | | | | 2/9 |
| 6,996,846 | B1 * | 2/2006 | Karapetyan | A41D 13/1184 |
| | | | | 2/10 |
| 2004/0065565 | A1 * | 4/2004 | Buesching | B65D 1/06 |
| | | | | 206/217 |
| 2004/0074498 | A1 * | 4/2004 | Begum | A41D 13/1192 |
| | | | | 128/206.21 |
| 2015/0034098 | A1 * | 2/2015 | Schumacher | A62B 23/025 |
| | | | | 128/863 |
| 2016/0213959 | A1 * | 7/2016 | Barklow | A41D 13/1107 |
| 2016/0332008 | A1 * | 11/2016 | McAndrews | A62B 18/084 |
| 2019/0008222 | A1 * | 1/2019 | Afjeh | A41D 27/08 |

* cited by examiner

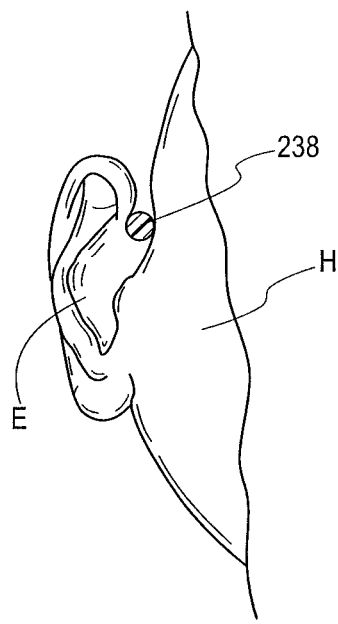
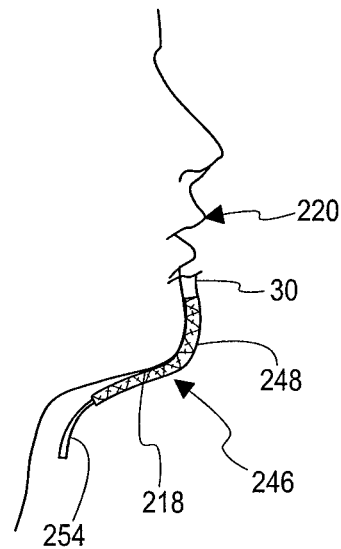
Fig. 36  Fig. 37
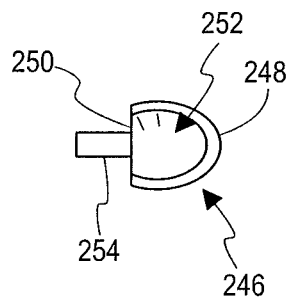
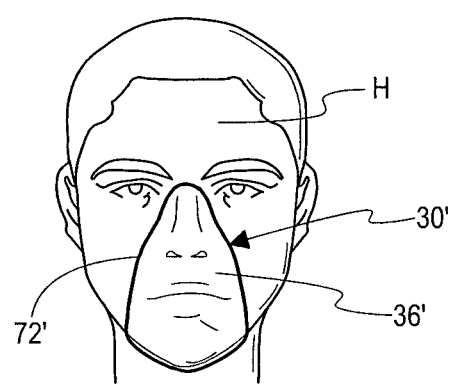
Fig. 38  Fig. 39

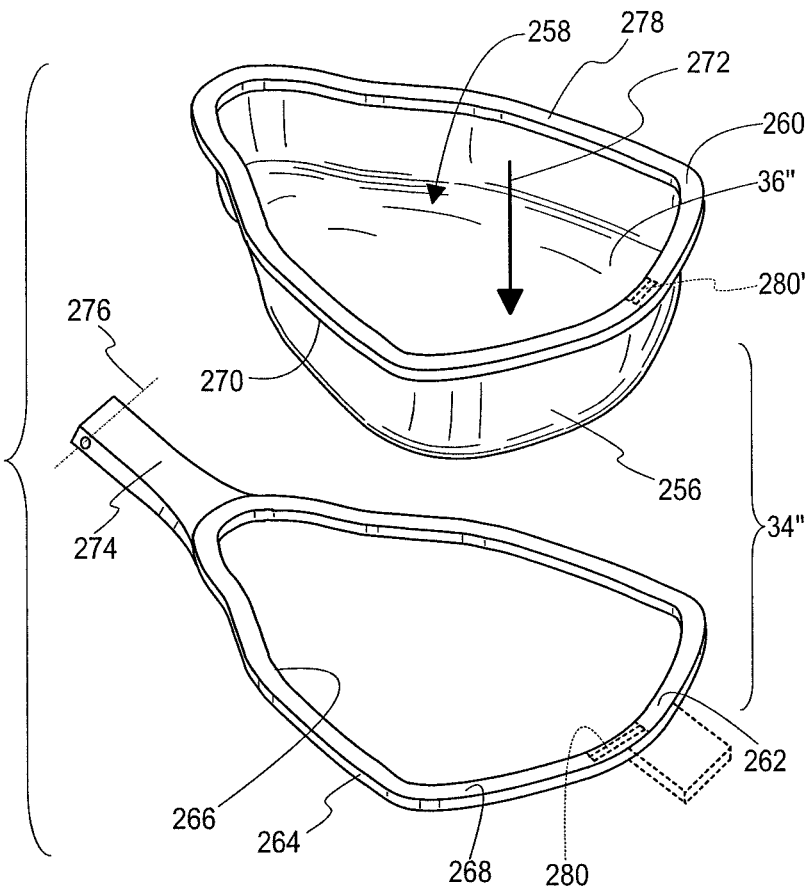
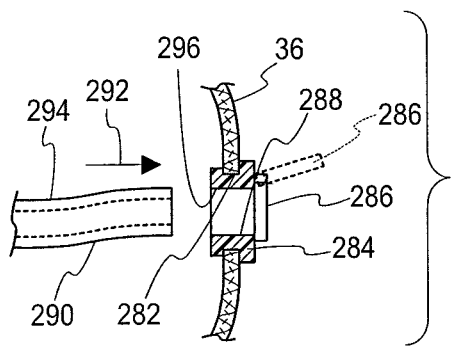
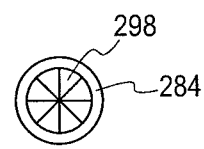
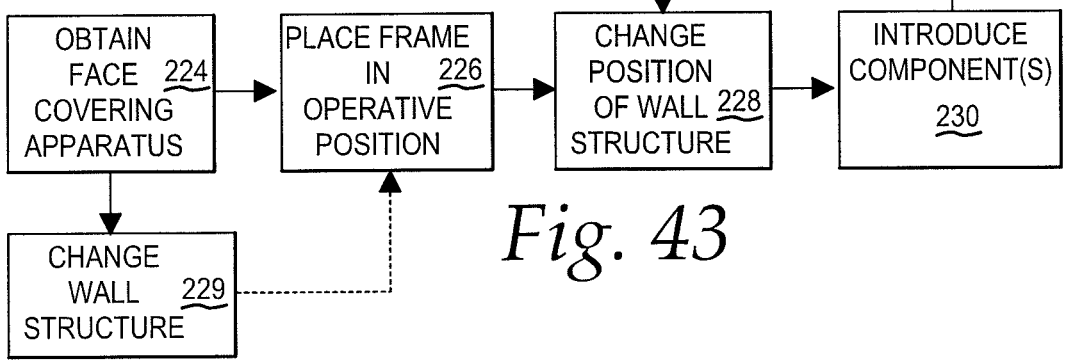
Fig. 40
Fig. 41
Fig. 42
Fig. 43

METHOD OF CONTROLLING TRANSMISSION OF PARTICLES TO AND AWAY FROM A PERSON'S FRONTAL FACE REGION

CROSS-REFERENCE TO RELATED APPLICATIONS

This application is a continuation-in-part of U.S. patent application Ser. No. 16/884,482 filed May 27, 2020, which claims priority to U.S. Provisional Application No. 63/006,813, filed Apr. 8, 2020, the disclosures of which are incorporated herein by reference.

BACKGROUND OF THE INVENTION

Field of the Invention

This invention relates to wearable devices and, more particularly, to a method of controlling transmission of particles to and away from a person's frontal face region using a wearable device.

Background Art

The coronavirus pandemic has effectively changed how future generations will behave and interact.

Heretofore, in the United States, surgical masks have been worn primarily by medical professionals in environments where avoidance of germ transmission is critical, such as during medical procedures and around individuals with conditions that make them highly vulnerable to contracting diseases or aggravating conditions. The same considerations have prompted a limited use of surgical-type masks by persons at high risk of contracting illness or in environments where a larger population sensitive to germs is present.

Surgical-type masks, or more sophisticated respiratory masks with filters, are also commonly worn in work environments where there is risk of inhalation of fumes, dust, and other particles that could lead to serious illness or other medical conditions.

In some countries, even outside air quality is such that surgical-type masks are a staple to at least limit particle inhalation that after extended periods could lead to respiratory problems or other dangerous health conditions.

However, most persons worldwide choose to travel freely and intermingle, commonly in close proximity to others, throughout daily work and recreational routines, without wearing any type of face covering. Aside from ignoring the consequences of inhaling germ-laden particles, individuals with an illness and in a contagious state, in settings where they are likely to transmit disease, generally do not utilize any type of face covering to avoid oral transmission of germs to surfaces or to other persons.

Generally, persons in most developed countries wearing surgical-type masks in public are viewed with a somewhat critical eye by a large portion of the population. Entering another person's surroundings with a surgical mask conveys the impression that the space is viewed as unsanitary or unsafe, which may be offensive to a hosting person or group.

Another reason that surgical-type masks are not worn regularly in public is that they are generally viewed as unfashionable. Most publicly available masks are bland in appearance and generally stand out against the rest of a person's garb. This problem is aggravated by the fact that the surgical-type masks are commonly held in place by thin elastic bands which cross the wearer's face and exert a pressure thereon that results in potentially long-lasting discolored impressions that stand out when the masks are removed. The tightened bands are also commonly wrapped against the wearer's ears, which is also inherently uncomfortable.

The conventional-type surgical mask also is not practically worn by persons in formal settings where makeup and jewelry are displayed. Further, voluminous hair makes it difficult to attach conventional masks, which also tend to undesirably alter the appearance of carefully coiffed hair.

While public scrutiny is not a problem with wearing surgical-type masks in the privacy of a home, most persons refrain from using such masks primarily due to the discomfort associated with the elastic mounting and the inconvenience of placing the masks on and removing the same—typically an exercise, often awkward, involving use of one, and more commonly both, of a wearer's hands. Whereas common sense would dictate that persons, cognizant of being contagious with transmittable illnesses, should cover their nose and mouths when in the vicinity of other persons in a shared space in their homes and when at risk of transferring germs to surfaces, such as during cooking, the inconvenience associated with such masks has severely limited their practical use.

The response to the coronavirus outbreak and the threat of encountering a future mutation has caused the entire world to take unprecedented precautionary steps throughout their every day to avoid germ transmission to and from surfaces and to and from other individuals who they are required to be in proximity with. While "social distancing" has addressed this problem to a certain degree, close human interaction is impossible to avoid. For example, work stations may be situated so that persons are sharing space in a confronting relationship closer than the currently recommended six foot minimal range. Seating in convention centers, restaurants, stadiums, airplanes, trains, buses, etc. is designed to compactly place individuals in spaces, which creates a constant risk of dangerous germ transmission.

As a practical matter, there currently is no way to motivate an entire group of closely situated individuals at, for example, sporting events, to each don some sort of protective headwear to minimize germ transmission. As noted, the primary barriers to such preventive measures are the generally unsightly nature of surgical-type masks, the inconvenience of putting the same on and taking the same off, and the discomfort associated with wearing conventionally designed surgical-type masks including uncomfortable elastic retention components.

At this point, there is no clear solution to the above problems, as a result of which it is inevitable that the precautionary steps taken to control a pandemic, once there is perception of an "all clear" state, will be abandoned by many in favor of comfort and convenience. As a result, the birth of another virus or the generation and transmission of a mutation of an existing virus is inevitable, with potentially future worldwide disruption of business and widespread health problems.

SUMMARY OF THE INVENTION

In one form, the invention is directed to a method for a person to control transmission of particles to and away from a frontal face region of the person. The method includes steps of: obtaining a face covering apparatus having: a) a frame configured to be releasably maintained in an operative position on the head of the person; and b) a covering assembly on the frame and having a wall structure; placing the frame in the operative position on the person's head by at least one of: i) resting the frame upon one or both ears of the person; and ii) causing the frame to frictionally engage a part of the person's head; with the frame in the operative position, placing the wall structure in a blocking position wherein the wall structure resides in paths of airborne particles moving: a) in a forward direction from the nostrils and/or mouth of the person; and b) in a rearward direction towards the person's nostrils and/or mouth; and with the frame in the operative position on the person's head, moving the wall structure guidingly in a predetermined manner from the blocking position into a staging position wherein the wall structure does not reside directly forwardly of the person's frontal face region below a horizontal plane at or above a top of the person's mouth.

In one form, with the frame in the operative position on the person's head and the wall structure in the staging position, the wall structure does not reside directly forwardly of the person's frontal face region below a horizontal plane at or above eyes of the person.

In one form, with the frame in the operative position on the person's head and the wall structure in the staging position, the wall structure does not reside directly forwardly of the person's frontal face region and below a plane containing a top of the person's ears adjacent the person's head and the bridge of the person's nose.

In one form, with the frame in the operative position on the person's head the wall structure moves through an angular range of in excess of 90° between the blocking and staging positions.

In one form, the method further includes a step of moving the wall structure guidingly in a predetermined manner from the staging position back into the blocking position.

In one form, the method further includes a step of introducing a component into at least one of the nostrils and mouth of the person with the frame in the operative position on the person's head and the wall structure in the staging position.

In one form, the wall structure has a pre-formed cup shape bounding a volume within which a nose of the person projects with the frame in the operative position on the person's head and the wall structure in the blocking position.

In one form, at least one of the covering assembly and the wall structure has a pear shape outline as viewed from a front perspective with the frame in the operative position on the person's head and the wall structure in the blocking position.

In one form, the wall structure has a rear edge extending around the volume. The step of moving the wall structure from the staging position back into the blocking position involves causing the rear edge to move against the person's frontal face region.

In one form, the step of moving the wall structure from the staging position back into the blocking position involves causing the rear edge to be biased against the person's frontal face region.

In one form, the rear edge has a pear shape as viewed from a front perspective with the frame in the operative position on the person's head and the wall structure in the blocking position. The person's mouth resides within the rear edge as viewed from a front perspective with the frame in the operative position on the person's head and the wall structure in the blocking position.

In one form, the rear edge has a formable shape. The rear edge is caused to re-shape and conform to a part of the person's frontal face region with the frame in the operative position on the person's head and the wall structure in the blocking position.

In one form, the wall structure resides fully above the wearer's eyes with the frame in the operative position on the person's head and the wall structure in the staging position.

In one form, the step of introducing a component consists of introducing edible material for consumption.

In one form, the frame supports at least one lens residing in front of eyes of the person with the frame in the operative position on the person's head.

In one form, the rear edge is caused to be biased against the person's frontal face region as an incident of the wall structure moving from the staging position into the blocking position with the frame in the operative position on the wearer's head.

In one form, the rear edge is caused to be biased against the person's frontal face region as an incident of at least one component being connected between the covering assembly and at least one of: a) the frame; b) a part of the person; and c) a structure on the person.

In one form, the step of placing the frame in the operative position consists of placing the frame in the operative position at an event. The step of obtaining a face covering apparatus consists of obtaining a face covering apparatus with information on the face covering apparatus relating to a product or service associated with the event and exposed and visible with the frame in the operative position on the person's head and the covering assembly in at least the blocking position.

In one form, the information is in the form of at least one of: a) at least one color; b) at least one word; and c) a logo.

In one form, the wall structure has a front surface. The information is provided on at least the front surface.

In one form, the step of obtaining the face covering apparatus consists of obtaining the face covering apparatus through a vendor at the event.

In one form, the event is one of: a) a sporting event; b) a social event; and c) a business event.

In one form, the event is a sporting event. The information relates to a team participating in the sporting event.

In one form, the information is in the form of an advertisement of a product or service.

In one form, the wall structure is a first wall structure. The method further includes a step of removing the first wall structure from the frame and replacing the first wall structure with a second wall structure.

In one form, the wall structure is a first wall structure. The method further includes the step of removing the first wall structure from the frame and replacing the first wall structure with a second wall structure. The first and second wall structures each has a front surface. The information on the first wall structure is on the front surface of the first wall structure. The second wall structure has information relating to a product or service associated with the event on the front surface of the second wall structure that is different than the information on the first wall structure.

In one form, the step of replacing the first wall structure consists of connecting the second wall structure to a maintained position on the frame through a press fitting step.

In one form, the method further includes the step of introducing a component into the mouth of the person through the wall structure with the frame in the operative position on the person's head and the wall structure in the blocking position.

In one form, the wall structure has a preformed cup shape with a rear edge. The method further includes the step of re-shaping the covering assembly including at least the rear edge to a selected configuration and moving the wall structure from the blocking position into the staging position with the selected configuration maintained.

In one form, the covering assembly has a discrete graspable tab. The method further includes the step of grasping the graspable tab and repositioning the graspable tab to change the wall structure between the blocking and staging positions.

BRIEF DESCRIPTION OF THE DRAWINGS

FIG. 36 is a fragmentary view showing a person's ear adjacent to the head whereat a part of a frame on the inventive face covering apparatus can be supported;

FIG. 37 is a fragmentary, side elevation view of a person's face with a component on a wall structure on the inventive face covering apparatus usable to releasably maintain the wall structure in a blocking position;

FIG. 38 is a plan view of the component in FIG. 37;

FIG. 39 is a front elevation view of a person with an exemplary inventive wall structure on the inventive face covering apparatus in a blocking position against a frontal face region of the person;

FIG. 40 is an exploded perspective view of a further modified form of covering assembly, according to the invention;

FIG. 41 is a fragmentary, partial cross-sectional view of a structure that allows passage of a component through a wall structure on the inventive face covering apparatus to facilitate consumption of an item with the wall structure in a blocking position;

FIG. 42 is a front/rear elevation view of a modified form of the structure as shown in FIG. 41; and FIG. 43 is a flow diagram representation of a method for a person to control transmission of particles to and away from his/her frontal face region, according to the invention.

DETAILED DESCRIPTION OF THE PREFERRED EMBODIMENT

Figure 1:
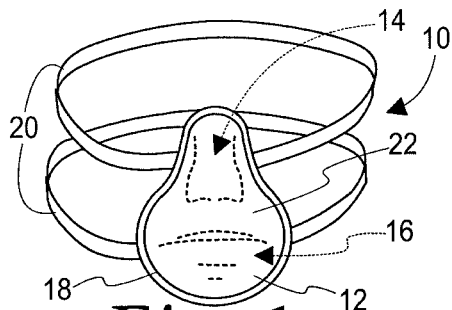
FIG. 1 is a perspective view of a conventional surgical-type mask shown in relationship to a wearer's nose and mouth.
Figure 2:
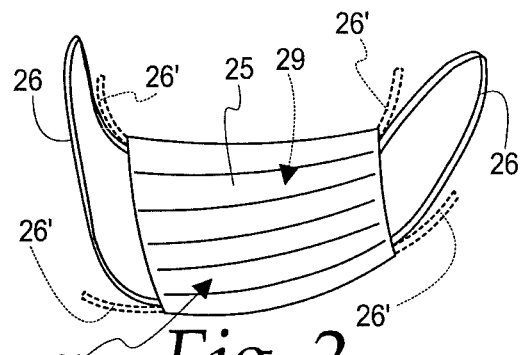
FIG. 2 is a view as in FIG. 1 of an alternative form of conventional surgical-type mask.

FIGS. 1 and 2 depict currently existing surgical-type masks of the general type to which the present invention is directed. In FIG. 1, a mask 10 has a cup-shaped body 12 which tapers upwardly and nominally conforms to a wearer's nose 14 and a wearer's face region around the mouth 16, as viewed from a front perspective. A perimeter edge 18, shown optionally outturned, will rest generally conformingly against the front region of a wearer's face with the mask being worn.

The body 12 is maintained on a wearer's head by elastic straps 20 which, in conjunction with the body 12, encircle a wearer's head, and biasably draw the body 12 rearwardly against the wearer's front facial region.

The body 18 has a continuous wall 22 made from one or more layers that allow air transmission therethrough while having certain filtering capabilities. While different materials are used for such walls, the fabrics commonly used have the ability to block passage of particles of certain size, including, for example, moisture droplets exhaled by the wearer. Other materials are used for purposes of solid particle control, vapor control, etc. Alternatively, only discrete regions may be provided that allow the passage of air to and from a volume bounded cooperatively by the wall 22 and the wearer's face.

The wall 22 is generally made with an upper width slightly greater than that of the wearer's nose and a lower width extending slightly beyond the opposite sides of the wearer's mouth. This allows a compact construction that is not onerous to the wearer yet may provide adequate protection in terms of preventing inhalation and exhalation of the targeted particle size and type.

The existing walls have different degrees of softness and abilities to maintain shape. They generally are pre-formed to define at least a shallow cup shape which might be reshaped upon being worn. Some are impressed with different shapes to increase stiffness, others use more rigid materials, while others use reinforcing elements.

The other prior art mask depicted in FIG. 2 at 24 consists of a generally flat, flexible body 25 with potentially overlapping, typically cloth, layers or a pleated construction which is placed against the mouth and the nose region of a user and drawn conformingly thereagainst by elastic straps 26, one at each side, which wrap around, and are drawn against, a wearer's ears.

Alternatively, vertically spaced strap lengths 26' are provided at each side, with the matching strap lengths 26' at opposite sides tied together and tightened to effect conforming of the body 25 to a wearer's face.

In another alternative form, the straps 26 may be arranged to wrap around a wearer's head as with the mask 10.

With the mask 24, the body 25 is of generally square or rectangular shape, in the latter case normally with the longer dimension arranged horizontally. The body 25 may be made from a single layer of material or using overlapped strips. In one form, the body 25 is made from one material that creates a receptacle 29 within which a potentially different type of material/layer with desired filtering characteristics is replaceably inserted.

As noted above, the masks of the type shown in FIGS. 1 and 2 generally rely upon an elastic biasing force, braced against a part of a wearer's head, to urge the bodies 12, 25 against a wearer's frontal facial region to at least a certain extent seal their perimeter regions to thereby limit the amount of particles that can be transmitted to and from a wearer's nose and mouth without encountering the filtering material making up the bodies 12, 25.

Given the small footprint of each of the depicted bodies 12, 25, the straps 20, 26, 26' in a tightened state are generally directly in contact with the wearer's skin, which can be irritating and which tends to create at least temporary depressions which may become unsightly and irritating until the wearer's tissue relaxes after the masks 10, 24 are removed. The straps 20, 26, 26' under tension may also be uncomfortable around the full circumference of a wearer's head. However, this problem persists so long as a fully surrounding, tightened arrangement is required for the masks 10, 24.

Figure 3:
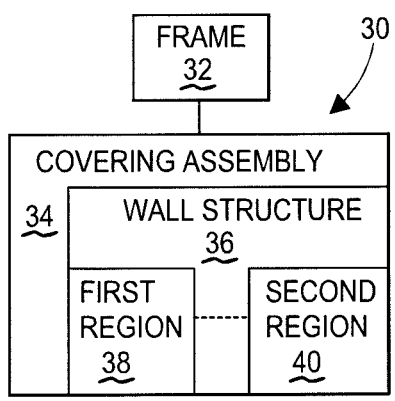
FIG. 3 is a schematic representation of a face covering apparatus, according to the invention, and consisting of a frame and a covering assembly with an associated wall structure.

In FIG. 3, a face covering apparatus, according to the present invention, is shown schematically at 30. The face covering apparatus 30 consists of a frame 32 configured to be placed in an operative position on a wearer's head and releasably maintained in the operative position by at least one of: a) resting upon one or both of a wearer's ears and b) frictionally engaging a part of the wearer's head.

The face covering apparatus 30 further includes a covering assembly 34 on the frame and having a wall structure 36 with: a) a first region 38 configured to conform to at least a part of a wearer's nose; and b) a second region 40 configured to conform to a wearer's face region around a wearer's mouth. The wall structure 36 may be continuous construction defining the first region 38 and second region 40, as indicated by the dotted lines, or such regions 38, 40 may be separate, coordinated parts as described below with respect to FIG. 15.

The face covering apparatus 30 is configured so that with the frame 32 in the operative position on a wearer's head and the wall structure in a blocking position on the frame, the first and second regions 38, 40 on the wall structure 36 together reside in the path of airborne particles moving: a) in a forward direction from a user's nostrils and/or mouth; and b) in a rearward direction towards a user's nostrils and/or mouth.

In various embodiments described herein, the wall structure 36 corresponds in shape to the prior art wall 22. This shape is not to be viewed as limiting as the perimeter shape, width, length, curvature, degree of forward projection, etc. might be changed. For example, the bottom of the wall structure 36 may extend up to the chin, around the chin, or terminate above the chin. The fore-and-aft depth may be selected to create a desired air volume between the front face region and the wall structure 36. Generally, the top region of the wall structure is desirably adjacent the bridge of the wearer's nose with the apparatus being worn. A compact design results with the perimeter of the wall/structure conformed relatively closely around a wearer's nose and mouth, particularly as seen from a front perspective. However, this shape and dimension is not required.

In one form, the frame 32 is configured to be moved from a position fully spaced from the wearer's head into the operative position by simply being translated relative to the wearer's head.

Figure 4:
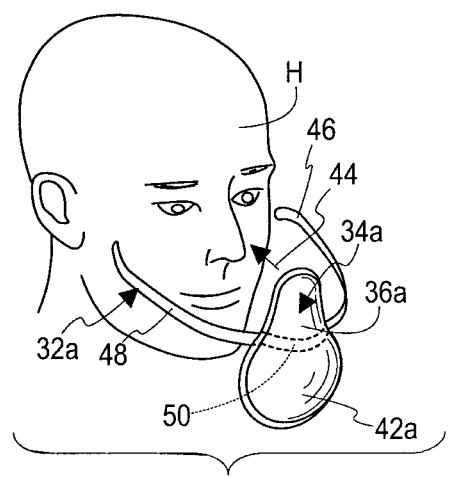
FIG. 4 is a perspective view of one form of face covering apparatus as shown in FIG. 3.

In one form, as shown in FIG. 4, the frame 32a defines, in conjunction with a body 42a on the covering assembly 34a, a "U" shape which can be aligned so that the plane of the U is horizontal and aligned in front of the wearer's head H as depicted in FIG. 4. By being translated horizontally from the spaced position in FIG. 4 in the direction of the arrow 44, legs 46, 48 engage and cooperatively squeeze the sides of the wearer's head to frictionally maintain the frame in its operative position, generally as do conventional headbands. As this occurs, the cup-shaped body 42a, which has generally the configuration of the body 12 on the prior art mask 10 and defines the wall structure 36a, is situated conformingly at the frontal region of the wearer's face over the nose and mouth, to thereby be in a blocking position in front thereof. The body 42a can have sufficient rigidity so that the body 42a, in conjunction with the legs 46, 48 defines the frame 32a. Alternatively, a reinforcing member 50 may be associated with the body to connect to the legs 46, 48 to define the frame 32a.

With this construction, the wearer is offered the convenience of effectively simply press fitting the wall structure 36a into the blocking position, which can be conveniently performed using a single hand. One or both of the legs 46, 48 may be stabilized by bearing on one or both of the wearer's ears.

At the same time, the frame 32a may be comfortably maintained in the operative position, wherein it positively supports the wall structure 36a in the operative position, potentially without any significant discomfort to the user. The depicted arrangement in FIG. 4 is similar to a frame on a pair of eyeglasses, which may be positively held in place without significant uncomfortable pressure on any part of a wearer's head. The engaging location for the legs 46, 48 may be above or below the ears and in the former case may, or may not, rest against the ears for support, stability, and/or fixation.

Figure 5:
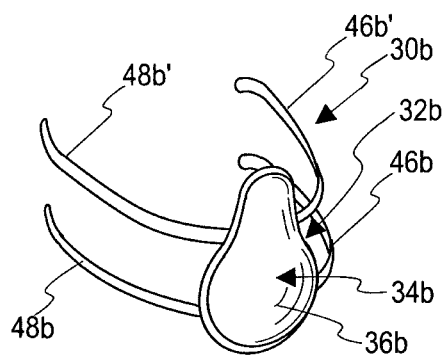
FIG. 5 is a view as in FIG. 4 of another form of face covering apparatus as shown in FIG. 3.

In FIG. 5, a modified form of the inventive face covering apparatus is shown at 30b and incorporates a leg pair 46b, 48b corresponding to the legs 46, 48 in the embodiment in FIG. 4, and an additional pair of legs 46b', 48b' creating a separate "U" closer to the nose location than the legs 46b, 48b, which are vertically in the vicinity of the mouth, whereby the wall structure 36b is stabilized at both regions. The additional legs 46b', 48b' add overall stability to the mounting of the covering assembly 34b without requiring greater force application to the wearer's head to maintain the frame 32b, made up of at least the legs 46b, 48b, 46b', 48b', in the operative position corresponding to that for the frame 32a in FIG. 4.

Figure 6:
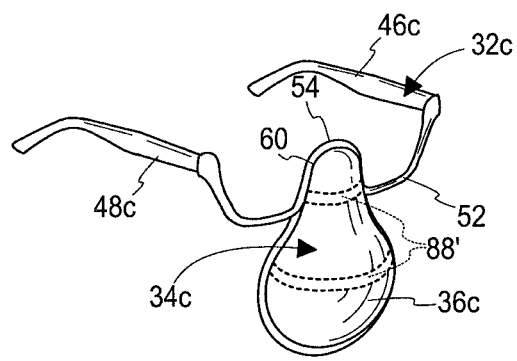
FIG. 6 is a view as in FIGS. 4 and 5 of another form of face covering apparatus as shown in FIG. 3.
Figure 7:
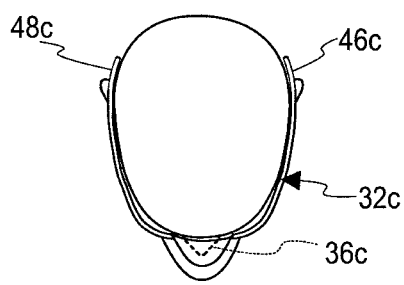
FIG. 7 is a plan view of the face covering apparatus in FIG. 6 with the frame thereon operatively positioned on a wearer's head.

In FIGS. 6 and 7, a further modified form of frame 32c is depicted having similarities to the frames 32a, 32b, however with the frame 32c shaped as a conventional eyeglass frame with legs 46c, 48c and a spanning frame portion 52 with a bridge part 54 that can be supported at a wearer's temple region as is typical of eyeglass frames.

In this embodiment, the wall structure 36c is connected to the frame portion 52, as at the part 54, in a depending fashion. Thus, with the frame 32c moved from a position fully spaced from a wearer's head into an operative position by front to rear translation, the wall structure 36c will be drawn into the blocking position around the wearer's nose and mouth region. The part 54 may be in front of the wall structure portion thereat so that the wall structure 36c is drawn captively against the wearer's face.

The connection between the frame 32c and wall structure 36c can be accomplished in a number of different manners. For example, as shown generally in FIG. 8, each covering assembly 34 may have a subframe 56 joined to the frame 32 using one or more connectors 57 on the frame 32 cooperating with one or more connectors 58 on the subframe 56.

As shown in FIG. 6, as an alternative to discrete type connectors, a part 60 of the wall structure 36c can be integrally formed with the frame 32c.

Figure 9:
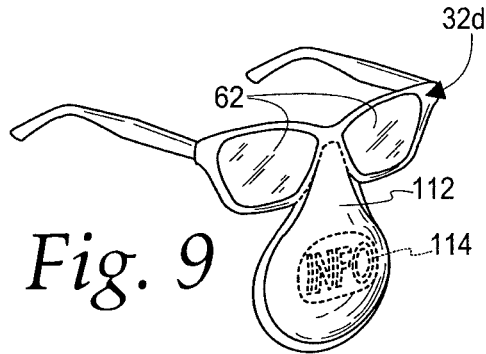
FIG. 9 is a view as in FIG. 6 of another form of face covering apparatus as shown in FIG. 3.

In FIG. 9, a modified form of frame 32d is shown, generally corresponding to the frame 32c, with the exception that the frame 32d has mounted lenses 62, which are situated in front of a wearer's eyes with the frame 32d in an operative position, corresponding to that shown for the frame 32c in FIG. 7. The lenses 62 may be made from a clear material without prescription, with a tinted surface to function as sunglasses, with a decorative see-through surface, or with a particular prescription, such as for reading or to correct for nearsightedness.

There is no limitation as to the connection between the frame 32 and wall structure 36 in the various embodiments. The connection may be permanent or one that is releasable, such as wherein the connectors 57, 58 in FIG. 8 allow for a snap fit, press fit, etc.

Figure 8:
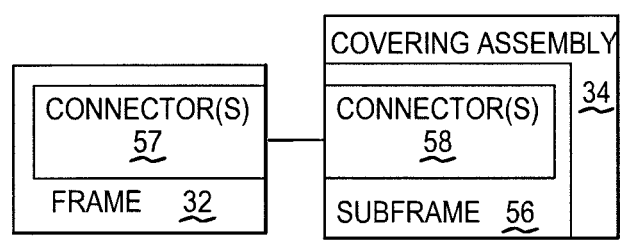
FIG. 8 is a schematic representation of a connection between the frame on the face covering apparatus in FIG. 3 and a subframe associated with the covering assembly.

The ability to connect and disconnect the covering assembly 34 as in FIG. 8 affords interchangeability of covering assemblies 34 and selection of covering assemblies 34 with different appearances, filtering capabilities, etc. Replacement of covering assemblies 34 past usable life is also facilitated.

Figure 10:
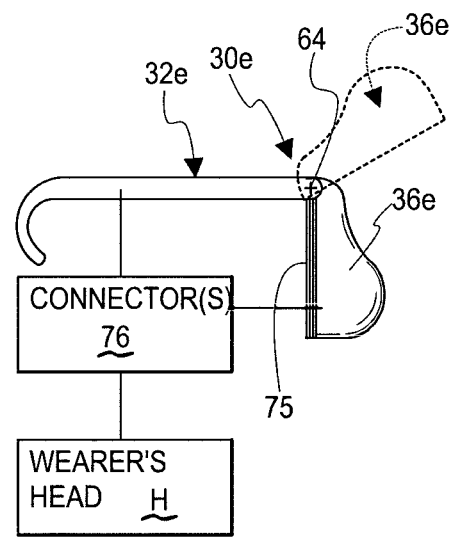
FIG. 10 is a side elevation view of another form of face covering apparatus as shown in FIG. 3 with the wall structure thereon in two different positions.

In FIG. 10, a further modified form of face covering apparatus is shown at 30e and consists of a frame 32e, as in the form of one of those described above or below, and incorporating a wall structure 36e that is repositionable relative to the frame 32e. Accordingly, with the frame 32e in an operative position on a wearer's head, the wearer has the option of maintaining the wall structure 36e in the blocking position, as shown in solid lines, or moving the same to a staging position, one of which is shown in dotted lines in FIG. 10, as might facilitate consumption of food or a beverage. In this embodiment, the wall structure 36e is pivotable around an axis 64 relative to the frame 32e. This may be accomplished by a fixed pivot axis as by using one or more pins, using a live hinge arrangement, or by other structure which may not be precisely characterized as a hinge but which allows a similar type movement.

Figure 11:
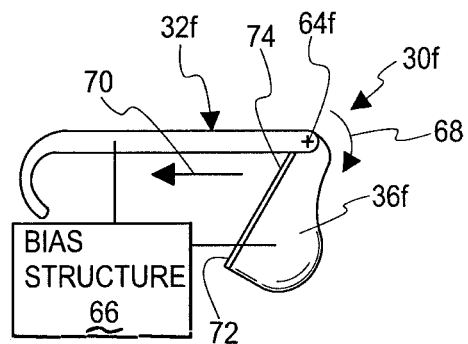
FIG. 11 is a view as in FIG. 10 of another form of face covering apparatus as shown in FIG. 3.

In FIG. 11, a modified form of face covering assembly is shown at 30f with a similar construction as the face covering assembly 30e, with the exception that a biasing structure 66 cooperates between the wall structure 36f and a frame 32f that generates a force tending to pivot the wall structure 36 around an axis 64f in the direction of the arrow 68. The bias may be generated through one or more tensioning components, cooperating ratchet or cam elements, etc.

Thus, as the face covering apparatus 30 is advanced from a fully separated position in the direction of the arrow 70 into its operative position, a wearer's face will contact the lower region of the wall structure 36f and progressively load the bias structure 66 so that a residual force urges the wall structure 36f in the pivot direction indicated by the arrow 68. In other words, the restoring force will urge the rear edge 72 of the wall structure 36f against the wearer's face to effect a more positive conformity and/or seal.

To provide better sealing between the wall structure 36f and the wearer's face, a flexible sealing component 74 may be applied at the edge 72 to be compressed between the edge 72 and the wearer's face. Alternatively, the edge material may itself be soft and conformable.

Still further, as shown in FIG. 10, accordion folds 75 may be incorporated to readily conform to different contours of the wearer's face.

In all embodiments the wall structure 36 may have an outturned edge that engages a wearer's face, or may be made without such an outturned edge.

In an alternative manner of enhancing this sealing effect, as shown in FIG. 10, one or more connectors 76 may be utilized to draw the wall structure 36e directly toward the wearer's head or indirectly through the frame 32e. The connector(s) 76 may have an elastic construction or may be otherwise constructed such as cooperating cam elements that interact to progressively hold with a greater force as the wall structure 36e is advanced towards/against a wearer's face.

Figure 12:
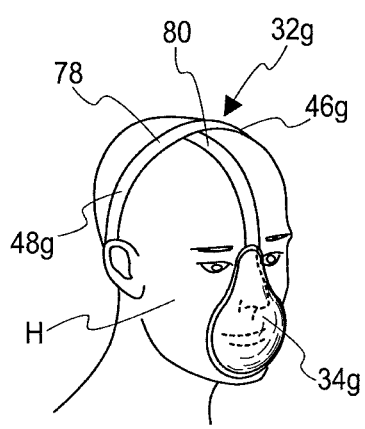
FIG. 12 is a perspective view of another form of face covering apparatus as shown in FIG. 3 with the frame operatively positioned on a wearer's head.

A further alternative frame construction is shown at 32*g* in FIG. 12. The frame has a U-shaped body 78 which is placed grippingly over a wearer's head H as a conventional headband by pressing the same from a fully separated position downwardly to cause legs 46*g*, 48*g* to straddle, and frictionally grip, the wearer's head. The body 78 has a support 80 which projects forwardly from the body 78. A covering assembly 34*g* is connected to the support 80 at a location forwardly from the body 78. The connection may be fixed, pivoted, etc.

Figure 13:
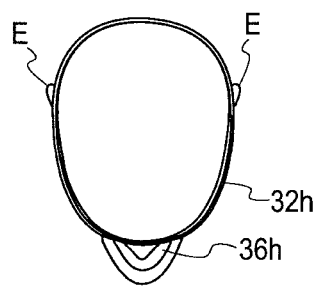
FIG. 13 is a view as in FIG. 7 with another form of the face covering apparatus in FIG. 3.

In FIG. 13, a frame 32*h* is shown with an associated wall structure 36*h*, and defines a substantially or fully continuous loop shape which can be directed downwardly over a wearer's head to frictionally grip the same to maintain the operative position therefor. Maintenance of the operative position may be assisted by bearing the frame 32*h* against one or both of the wearer's ears E.

Figure 14:
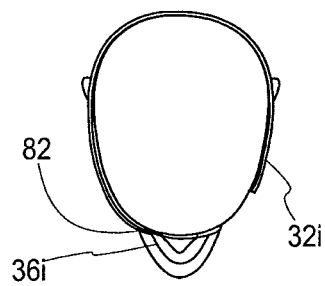
FIG. 14 is a view as in FIG. 13 with still another form of face covering apparatus as shown in FIG. 3.

In FIG. 14, a further modified form of frame 32*i* is shown wherein the frame 32*i* does not extend fully around the wearer's head so that a wall structure 36*i* is cantilever mounted adjacent an end 82 of the frame 32*i*. This configuration corresponds to another known manner of mounting eyeglasses, wherein the frame wraps around the back of a wearer's head and embraces the sides of the wearer's head to be maintained in place.

It should be understood that the various frame configurations described hereinabove are representative in nature only. The schematic depiction of the face covering apparatus 30 encompasses each of such versions and variations of each of the components therein and their interactions.

Figure 15:
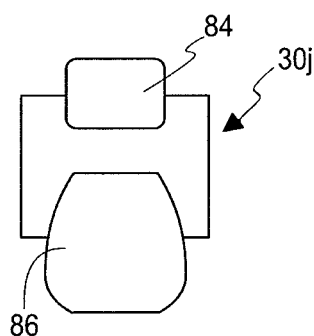
FIG. 15 is a schematic representation of a modified form of wall structure as shown in FIG. 3.

Some additional aspects of different embodiments will now be described. For example, as shown in FIG. 15, while the configuration of the wall structures 36 described has been described above to be generally the same as the wall structure in the prior art mask 10, this is not a requirement. This same general shape is desired because of its effective coverage while being compact in nature. In FIG. 15, the face covering apparatus 30*j* consists of separate wall parts 84, 86 which cooperative perform the function of the aforementioned wall structure 36. The wall portions 84, 86 may be connected to each other or independently connected to any of the contemplated frame constructions. The wall portion 84 defines the corresponding region 38 for the nose region, whereas the wall portion 86 defines the corresponding second region 40 for the mouth region, as indicated in the schematic showing in FIG. 3.

Figure 16:
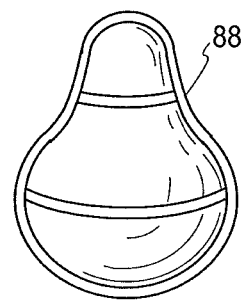
FIG. 16 is a perspective view of a subframe making up part of a wall structure as shown in FIG. 3.
Figure 17:
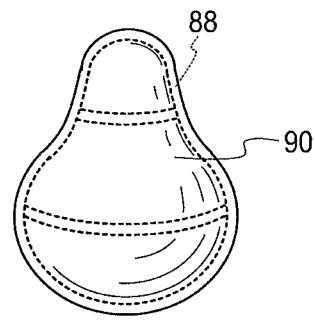
FIG. 17 is a view as in FIG. 16 with a filter layer applied to the subframe.

In each embodiment, the wall structure 36 may be made from a substantially rigid material that maintains shape and facilitates its mounting to its respective frame, or be made with a subframe 88, as shown in one exemplary form in FIGS. 16 and 17, that has a more rigid construction that holds shape and lends itself to stable connection to one of the frame configurations. As shown, the subframe 88 has a skeletal shape preformed to the desired end shape for the wall structure 36. Filtration can be carried out by applying one or more layers 90 of suitable construction over the subframe 88 at the front and/or the rear side of the subframe 88. The subframe 88 may be made with a construction that allows reshaping and maintenance of a selected reconfigured shape.

The subframe 88 need not extend fully around the perimeter of the associated cover assembly.

Figure 18:
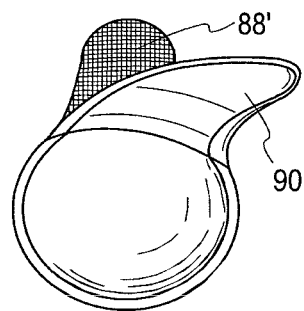
FIG. 18 is a view as in FIGS. 16 and 17 of a modified form of subframe with a filter layer partially peeled away therefrom.

In an alternative construction as shown in FIG. 18, a subframe 88' consists of a formable, preferably metal mesh-type material which has sufficient rigidity to maintain different selected shapes but which at the same time may be conformable enough to allow a complementary shape to each user's face to be selected. As in the prior embodiment, one or more layers 90 can be suitably applied to the front and/or the rear of the subframe 88'.

Figure 19:
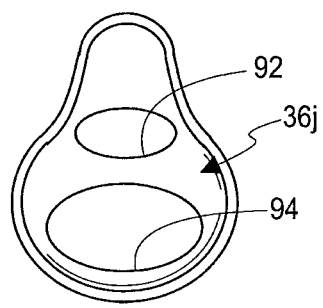
FIG. 19 is a view as in FIGS. 16-18 and showing a further modified form of wall structure as shown in FIG. 3.

In an alternative construction, as shown in FIG. 19, a wall structure 36*j* has a substantially rigid nonporous shape with strategically located openings 92, 94 formed therein which can be covered by an appropriate filtering material.

Figure 20:
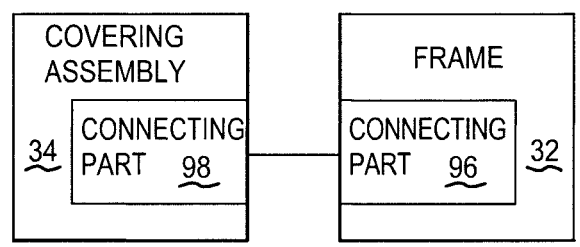
FIG. 20 is a schematic representation of a connection between the frame and covering assembly as shown in FIG. 3.

The connection between the frame 32 and covering assembly 34 is not limited to requiring a subframe. As shown in FIG. 20, the invention contemplates any type of joining of the covering assembly 34 and frame 32 by utilizing any configuration of cooperating connector parts 96, 98, respectively on the frame 32 and covering assembly 34. Slide fit or snap fit connectors may be desirable to allow simple and quick replacement of covering assemblies to change look or to substitute clean or different types of covering assembly 34.

Figure 21:
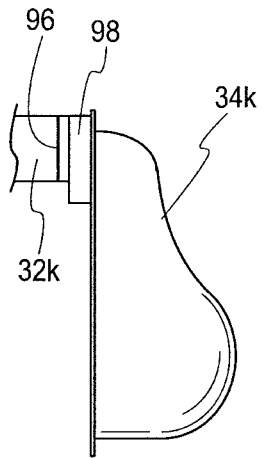
FIG. 21 is a side elevation view of one specific form of connection between a frame and wall structure as shown in FIG. 3.

For example, as shown in FIG. 21, a covering assembly 34*k* is shown with the connector part 98 separately attached thereto that is suitably joined by the connector part 96 on the frame 32*k*. The connection may be releasable or permanent, one that fixes the relationship of the frame 32*k* and covering assembly 34*k'*, or one that allows relative movement therebetween, etc.

The connector 98 may function as part of the aforementioned subframe 56 or may be considered a separate part therefrom.

As noted above, it is also contemplated that one piece may define part of the frame 32 and covering assembly 34 to facilitate stable maintenance of the wall structure 36 on the frame 32.

Figure 22:
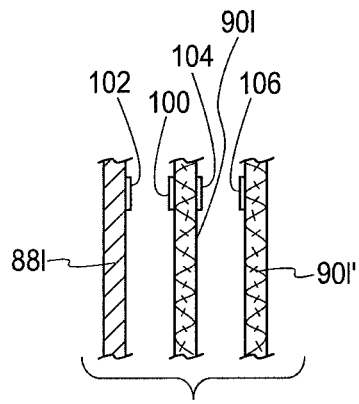
FIG. 22 is a fragmentary, exploded view showing a subframe as in FIG. 16 with multiple filter layers applied thereto.

As shown in FIG. 22, a subframe 88*l* may use cooperating connectors 100, 102 to maintain a layer 90*l* against the frame 88*l*. In turn, cooperating connectors 104, 106 may cooperate to maintain a layer 90*l'* stacked upon the layer 90*l* to achieve a cumulative filtering effect.

Figure 23:
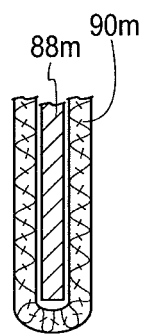
FIG. 23 is a fragmentary, sectional view showing a filter layer connected to a subframe in an alternative manner to that shown in FIG. 22.

In FIG. 23, a filtering layer 90*m* is wrapped around a subframe 88*m* to operatively maintain the layer 90*m* thereon.

Figure 24:
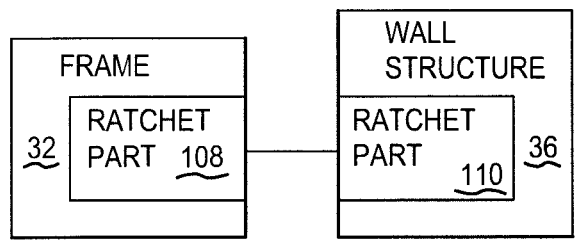
FIG. 24 is a schematic representation of a ratchet connection between a frame and wall structure as shown in FIG. 3.

In FIG. 24, another optional feature is disclosed which allows the wall structure 36 to be repositioned and maintained in different positions relative to the frame 32. As depicted, there are cooperating ratchet parts 108, 110, respectively on the frame 32 and wall structure 36, that permit the wall structure 36 to be moved in stepwise fashion with each of the different positions maintained by the ratchet parts 108, 110. Such an arrangement, while not so limited, is particularly adaptable to the face covering apparatus 30*e*, 30*f* in FIGS. 10 and 11, respectively, and may be used to enhance sealing.

Figure 25:
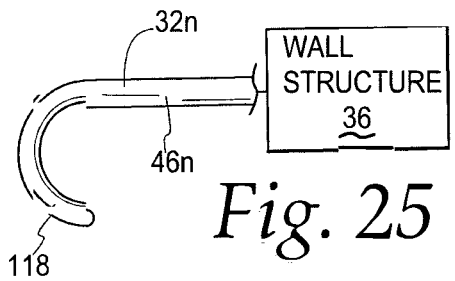
FIG. 25 is a fragmentary, side elevation view of a modified form of arm as usable on frame configurations as in FIGS. 6 and 9.

In FIG. 25, one modification is shown usable with embodiments wherein the frame has legs 46, 48. An exemplary one of the legs 46*n* may have a turned end 118 which can be wrapped against a wearer's ear and can be configured to positively hold the leg 46*n* in a rearward position which positively holds the associated frame 32*n* in place and allows a preloading of the particular wall structure 36 against the wearer's front facial region.

In another variation, as shown in FIG. 6, the aforementioned concept of the subframe 88 may be incorporated, as shown at 88', in the form of discrete subframe components that are strategically placed and have a deformable construction that is shape retentive to allow local shaping of the wall structure 36*c* for better comfort, conformability, and sealing.

Figure 26:
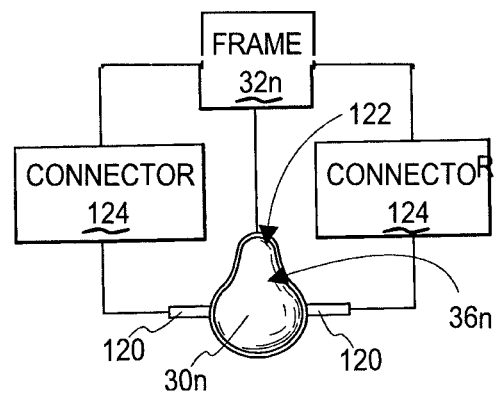
FIG. 26 is a partially schematic, front elevation view of another form of face covering apparatus, as shown in FIG. 3.

In FIG. 26, a further modified face covering apparatus is shown at 30*n*, consisting of a wall structure 36*n* with associated adapters 120 which facilitate supplemental reinforcement of the wall structure 36n against the frame 32n. As shown, the wall structure 36n is connected at one location 122 to the frame 32n. Through the adapters 120, one or more connectors 124 can be joined between the adapters and frame 32n at locations spaced from the location 122.

Without limitation, as one example, the connection at the location 122 may be of the type shown in FIG. 10 or 11, with the connectors 124 each in the form of a biasing component, such as one that is elastic, that produces the aforementioned biasing force tending to pivot the wall structure 36n in the direction indicated by the arrow 68 in FIG. 11.

Supplemental rearward biasing of the wall structure 36n, and other wall structures 36 herein, may be achieved by a direct connection between the apparatus 10 and the wearer.

Figure 27:
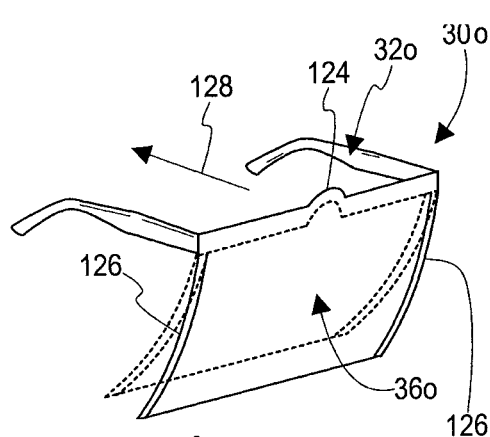
FIG. 27 is a view as in FIGS. 6 and 9 of another form of face covering apparatus as shown in FIG. 3.

As shown at FIG. 27, the face covering apparatus 30o supports a flexible wall structure 36o of the type shown in FIG. 2 made with a sheet or layer that is non-shape retentive and draped against a wearer's face.

The perimeter portion of the wall structure 36o can be attached to the frame 32o, shown with a bridge mount 124 and depending legs 126 which support the wall structure 36o such that it will be drawn conformingly against the wearer's front facial region as the frame 32o is advanced towards its operative position in the direction of the arrow 128.

Figure 28:
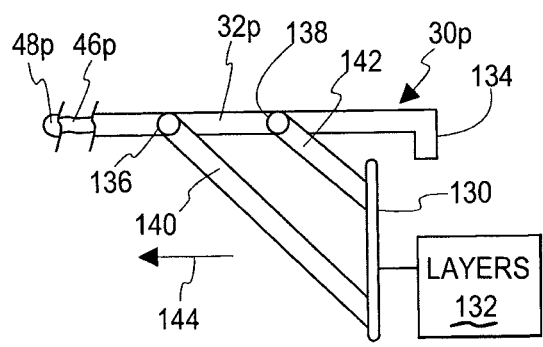
FIG. 28 is a side elevation view of another form of face covering apparatus as shown in FIG. 3.

In an alternative form, as shown in FIG. 28, a subframe 130, consisting of one continuous member or spaced members at opposite sides of the frame, may be used to support one or more layers 132 making up a wall structure as shown in FIGS. 2 and 27. The subframe 130 is mounted on a frame 32p with a temple support 134 and legs 46p, 48p which cooperatively straddle a wearer's head.

Exemplary leg 48p has mounts at locations 136, 138, which respectively support biasing/elastic components 140, 142 extending between respective mount locations 136, 138 and the subframe 130.

As the frame 32p on the face covering assembly 30p is advanced rearwardly towards an operative position, as indicated by the arrow 144, the wearer's face bears against the layers 132 and loads the elastic elements 140, 142 whereby the layers 132 are drawn biasably against a wearer's frontal region to conform thereto.

Figure 29:
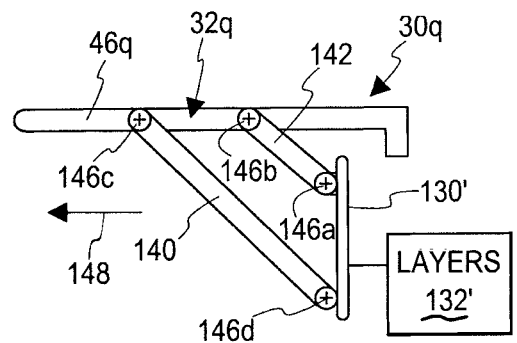
FIG. 29 is a view as in FIG. 28 of yet another form of face covering apparatus as shown in FIG. 3.

In FIG. 29, an apparatus 30q with a similar arrangement as in FIG. 28 is shown wherein a frame 32q uses mechanical linkages 140, 142 at each side, shown in FIG. 28 connecting between the exemplary leg 48q and subframe 130' at one side of the frame 32q. As depicted, the links 140, 142, subframe 130', and leg 48q are connected through spaced pivot connections with axes 146a, 146b, 146c, 146d which allow the layers 132', held in the depending fashion on the subframe 130', to orient over the nose and mouth as the frame 32q on the face covering apparatus 30q is advanced rearwardly in the direction of the arrow 148, causing the supported layers 132' to conform to the wearer's face at the nose and mouth.

The connection at the pivot axes 146 may be unrestrained or there may be a pre-biasing structure incorporated to simulate the function of the FIG. 28 structure, as by using torsion coil springs.

Figure 30:
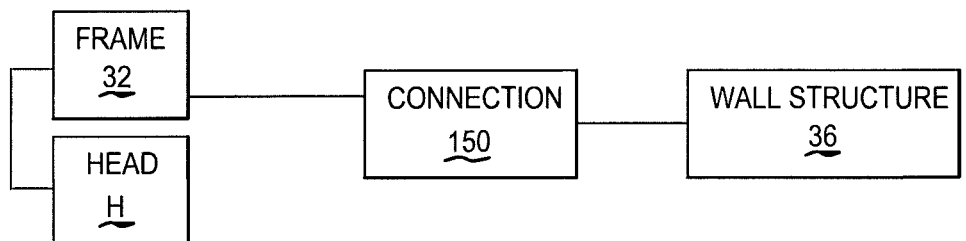
FIG. 30 is a schematic representation of another form of face covering apparatus, according to the present invention.

Generally, as shown in FIG. 30, with each embodiment disclosed, and others contemplated, the frame 32 provides the primary mount for each wall structure 36. By placing the frame 32 in the operative position, the wall structure 36 may be held through an appropriate generically identified connection at 150 in the blocking position on the frame directly in front of the nostrils and mouth of a wearer. As noted above, and in the basic construction, even in a loose, non-sealing arrangement, the wall structure 36 in the blocking position defines a barrier to direct passage of particles horizontally to and from the wearer's nostrils and mouth.

By reason of permitting, but not requiring, the frame 32 to be mounted as described in the specific embodiments described herein, a user may be able to place the frame 32 in an operative position as he/she would place eyewear and headbands—with a single hand. The single movement may finally seat the wall structure 36 or may conveniently support the wall structure 36 for augmented connection to the frame 32 and/or the wearer's head H.

With this basic construction, different versions of face covering apparatus can be developed from a very simple, lightweight structure that provides an unsealed wall structure that blocks horizontal passage of particles to and from the nostril and mouth regions, to a more conformed and sealed arrangement which may be effected as an incident of placing the frame in the operative position or enhanced by further adjustments and use of additional connecting structure. Once the frame is in the operative position, this augmentation of sealing may be made possible by one hand, thereby obviating the need to employ both of the wearer's hands to implement the face covering apparatus. This augmentation may involve manipulation of the apparatus 10 and/or effecting a further connection directly between the apparatus 10 and wearer.

While there is no specific limitation as to the shape and dimensions of a wall structure or with respect to the at least a partially preformed shape as shown in FIG. 5, typically the dimensions will be such as to conform generally to the nose and mouth region as shown for the prior art mask 10 in FIG. 1. This allows the nose to nest within the relatively narrow first region 38, with the region at/above the wearer's chin nesting in the second region 40 without the requirement of significant projection of the wall structure forwardly beyond the wearer's face or significantly above the wearer's nose, which might interfere with a wearer's vision, both in forward and downward directions. The peripheral wall region that engages a wearer's face may be soft and flexible or made more rigid as by selecting an appropriate material, processing a material, and/or by using reinforcement structure, as described above.

With the various embodiments described above, it is possible for the wall structures to be maintained in their blocking positions directly in front of the user's mouth and nostrils without causing discomfort to the wearer. At the same time, the frames can be readily placed in their operative positions and removed therefrom with minimal inconvenience and in most cases by using a single hand. Thus, one has the convenience of picking up the face covering apparatus as he/she would a pair of eyeglasses and placing the frame in an operative position with a simple movement that may not require manipulation of elastic straps and bulky head mountings.

To address the stigma associated with wearing surgical masks in public and to promote healthier habits on an ongoing basis, the face covering apparatus 30 can be made both functional and decorative beyond its basic particle blocking function. In the one embodiment, described above, the wall structure can be integrated into eyeglasses.

To further promote wearing of protective structures, as shown in exemplary FIG. 9, the exposed surface 112 in that embodiment can be adorned with artistic designs or with information in the form of logos, advertising, identifying colors/coloring, etc. This information is identified generically in FIG. 9 as "info" at 114 and preferably occupies at least 50% of the exposed area thereof.

This latter construction can be used beneficially at events wherein a large number of attendees are anticipated. For example, at a baseball game, where seats are compactly stacked and people are moving in close proximity to each other in different facing relationships, a face covering apparatus such as that in FIG. 9 could be supplied as a souvenir item. The information 114 may be in the form of a team logo/color that will inspire people to make a purchase for utility and to have retainable memorabilia.

Even at conferences, as in group meeting rooms, a company's logo may be applied as the "info" to promote teamwork while at the same time addressing health issues.

In a more general sense, in the public, creative adornment on the exposed surfaces may make individuals more comfortable wearing the same consistent with fashion, as opposed to the impression currently conveyed of an individual coping with a dangerous environment.

Figure 31:
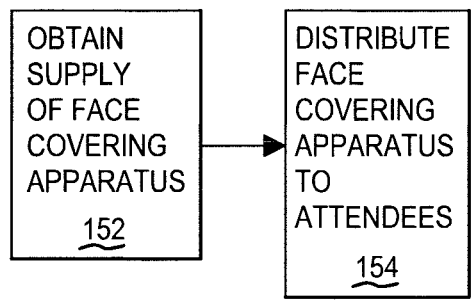
FIG. 31 is a flow diagram representation of a method of equipping attendees at an event to reduce transmission of particles, according to the invention.

With the above-described structure, a method of equipping attendees at an event to reduce oral transmission of particles can be carried out as shown in flow diagram form in FIG. 31.

As shown at block 152, a supply of face covering apparatus, as described above, is obtained, wherein the wall structure has a forwardly facing surface with information pertaining to the event visibly placed thereon.

As shown at block 154, the face covering apparatus are distributed to attendees of the event to be worn during the event.

As noted above, the information may be related to the event and may include a logo associated with a team or an entity sponsoring or participating in the event.

Alternatively, the information may be an advertisement for a product or service, related or unrelated to the event.

The apparatus may be provided gratuitously or sold as a revenue generator.

By providing a generic frame construction with interchangeable wall structures, vendors can keep on hand wall structures/coverings assemblies with different appearances. For example, vendors at baseball games can provide wall structures with different team logos as different teams play at that particular venue.

More generally, a manufacturer can offer a generic frame with virtually an unlimited number of differently ornamented wall structures and wall structures that have different information thereon which may be included for entertainment and/or function.

Figure 32:
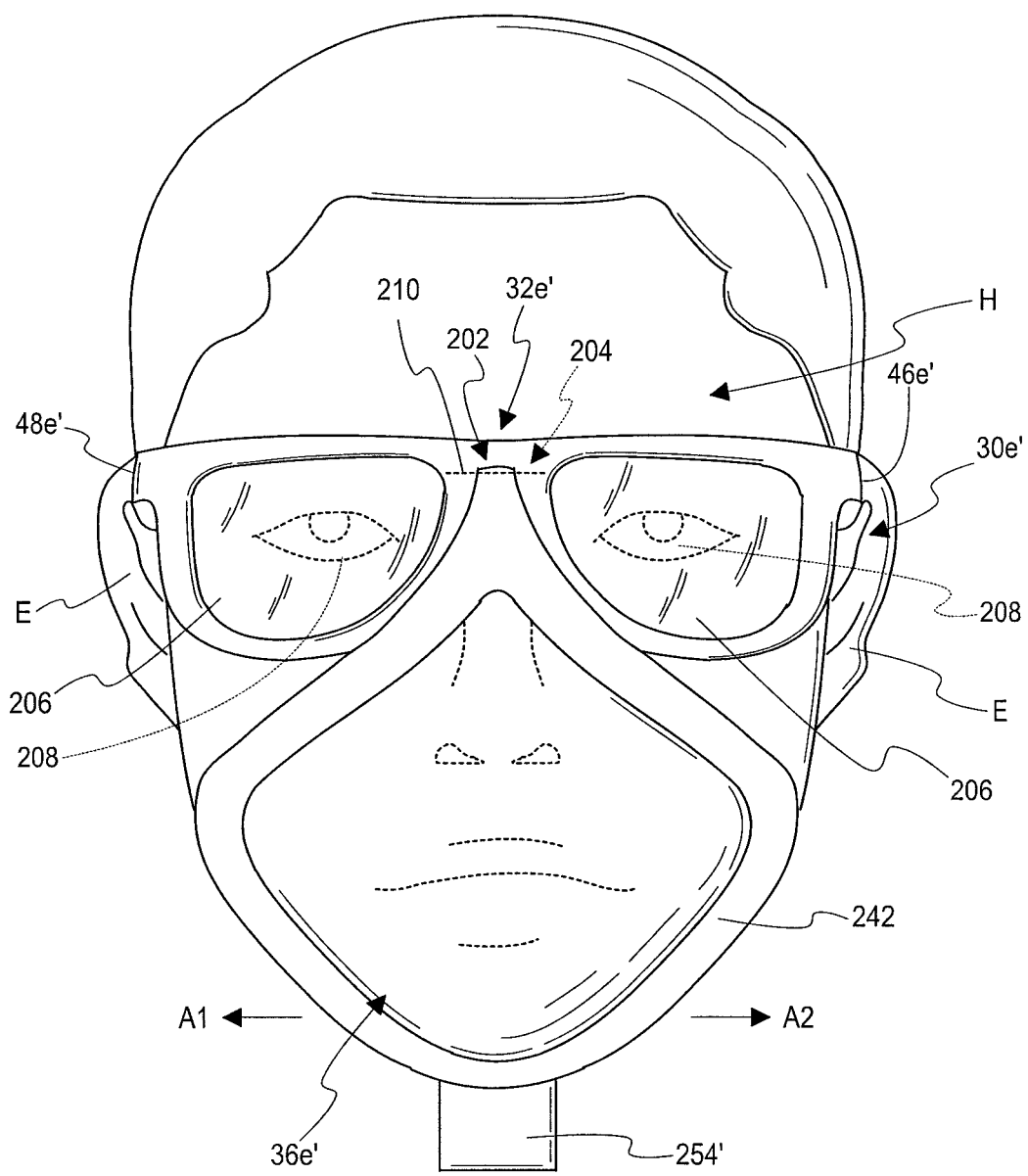
FIG. 32 is a front elevation view of a further modified form of face covering apparatus, according to the invention, on a wearer's head and with a wall structure thereon in a blocking position.
Figure 33:
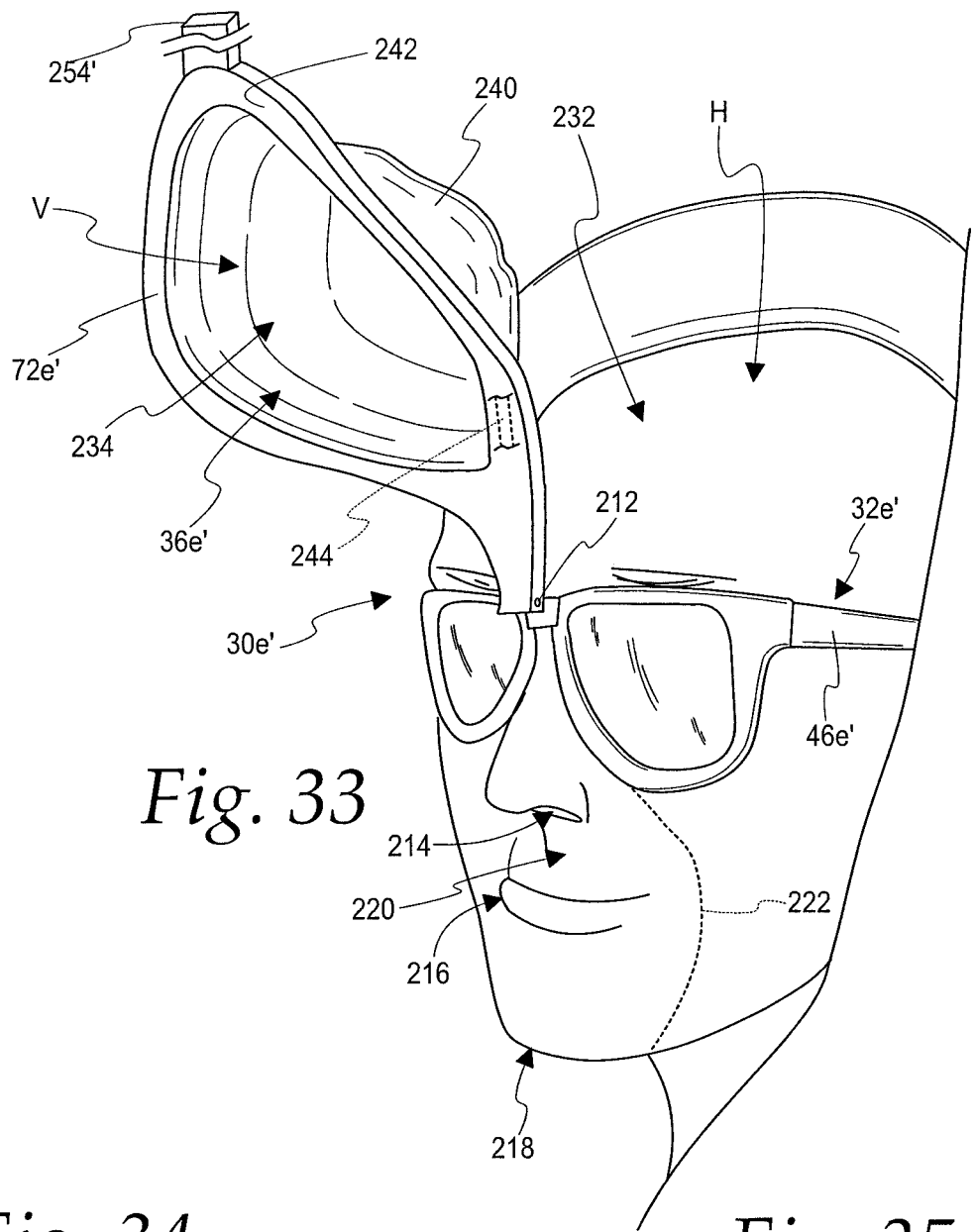
FIG. 33 is a fragmentary, perspective view of the wearer's head with the wall structure in FIG. 32 moved to a staging position.

In FIGS. 32 and 33, another form of face covering apparatus, corresponding generally in function to the face covering apparatus 30e, 30f in FIGS. 10 and 11, and potentially including structures from other embodiments herein, is shown at 30e'. The frame 32e' has a conventional eyeglass frame construction and is shown as worn in conventional fashion with: a) legs 46e', 48e' resting on each of the person's ears E and cooperatively straddling the person's head H; and b) a front bridge portion 202 on the frame 32e' resting on the person's nose bridge at 204.

In this embodiment, the frame supports two lenses 206, with one each in front of an eye 208 of the person. The lenses 206 could be clear or shaded, with or without prescription, etc. Alternatively, the frame 32e' may be made without any lenses.

A wall structure 36e' on the face covering apparatus 30e' is mounted to the frame 32e', in this exemplary embodiment, at the bridge portion 202, for pivoting movement around an axis 210, as through one or more pins 212. The axis 210 extends substantially horizontally and in a lateral direction.

As in the prior embodiments, with the frame 32e' in the operative position of FIGS. 32 and 33, the wall structure 36e' can be placed in a blocking position, as shown in FIG. 32, wherein the wall structure 36e' resides in paths of airborne particles moving: a) in a forward direction from the nostrils 214 and/or the mouth 216 of the person; and b) in a rearward direction towards the person's nostrils 214 and/or mouth 216. In this embodiment, the wall structure 36e' depends downwardly to, or below, the person's chin 218 with the rear edge 72e' generally conforming to the contours of the wearer's frontal face region at 220 with a footprint generally as indicated by the dotted lines 222 in FIG. 33.

Starting with the frame 32e' in the operative position on the person's head, the wall structure 36e' can be moved guidingly in a predetermined manner from the blocking position of FIG. 32 into a staging position, as shown in FIG. 33, wherein the blocking portion of the wall structure 36e' moves to above the top of the frame 32e' so as not to obstruct a person's forward and lateral vision.

At the same time, the nose and mouth regions are unobstructed directly forwardly thereof by the wall structure 36e' as a result of which the person is free to eat and drink in normal fashion, as by using utensils, cups, bottles, etc., potentially without interference from the wall structure 36e'.

FIG. 43 schematically depicts the steps associated with a method for a person to control transmission of particles to and away from the frontal region of the person.

As shown at block 224, a face covering apparatus, such as the face covering apparatus 30e' in FIGS. 32 and 33, is obtained, as at a sporting event or another venue where food and/or drink are offered.

As shown at block 226, the frame 32e' on the face covering apparatus 30e' is placed in the operative position.

As shown at block 228, the person changes the wall structure 36e' from the blocking position of FIG. 32 into the staging position of FIG. 33.

As shown at block 230, with the wall structure 36e' in the staging position, the person introduces an item/component into at least one of the person's nostrils 214 and/or mouth 216.

After introducing the item(s)/component(s), the person moves the wall structures 36e' guidingly in a predetermined manner from the staging position of FIG. 33 back into the blocking position of FIG. 32, as indicated by block 228 in FIG. 43.

As explained below, the wall structure 36e' can be changed, as shown at block 229.

The degree of movement between the blocking and staging positions and the precise situation of the wall structure 36e' relative to the person's frontal face region 220 may be different while still maintaining desired function.

With the structure in FIGS. 32 and 33, the wall structure 36e' may be pivoted as far back as to contact the person's forehead 232 in the staging position, wherein a cup-shaped portion 234 of the wall structure 36e' opens forwardly or forwardly and downwardly, but in any event is substantially above the wearer's eye location.

The particular wall structure 36 (generic to all such movable wall structures) may move guidingly in a predetermined manner initially away from the frontal face region 220 of the person and upwardly to clear different regions therebelow directly in front of the person.

Figure 34:
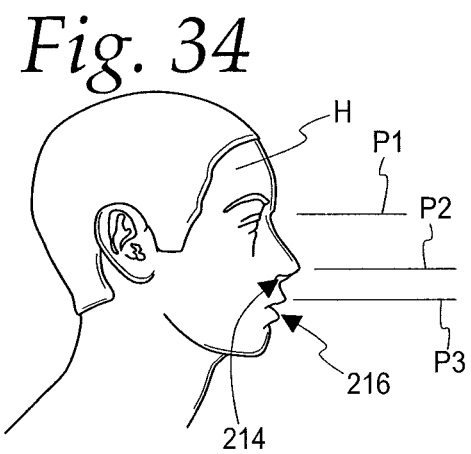
FIG. 34 is a side elevation view of a person's head with three different reference planes relating to three different staging positions for the wall structure on the inventive face covering apparatus when worn by the person.

In FIG. 34, there are three different horizontal reference planes depicted. In one form of the face covering apparatus, with the generic frame 32 in the operative position on the person's head and the wall structure 36 in the staging position, the wall structure 36 does not reside directly forwardly of the person's frontal face region below the horizontal plane P1, which is at or above the person's eyes.

Reference planes P2 and P3 are respectively above the person's nostrils 214 and the person's mouth 216.

Figure 35:
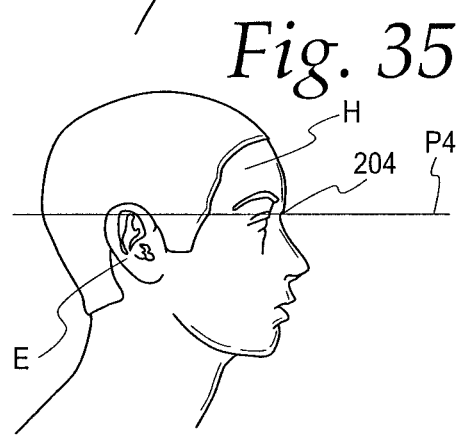
FIG. 35 is a view as in FIG. 34 with an alternative horizontal reference plane.

The face covering apparatus may be designed with a specific relationship to an alternative horizontal plane P4, as shown in FIG. 35, which extends from the top of the person's ears E adjacent the person's head H, and the person's nose bridge 204.

The noted location at the "top" of the person's ears E adjacent the person's head H is shown in FIG. 36, wherein an exemplary frame leg 238 is nested in a seat defined by the ear E and head H to accommodate conventional eyeglass frames.

Thus, in FIG. 35, the face covering apparatus 30 can be designed so that with the frame 32 in the operative position on the person's head and the wall structure 36 in the staging position, the wall structure does not reside directly forwardly of the person's frontal face region 220 below the plane P4.

Another design parameter may be to have the frame 32 move through an angular range of in excess of 90° between blocking and staging positions.

While not a requirement, as shown in FIG. 39, in one preferred form at least one of the wall structure 36' and covering assembly 30' has a pear-shaped outline as viewed from a front perspective with the frame (not shown in FIG. 39) in the operative position and the wall structure 36' in the blocking position.

The "pear shape" is intended to encompass a structure that is narrower in the nose region and widens therebelow. The shape may be rounded or more squared, as shown for the wall structure 36e' in FIGS. 32 and 33.

In the embodiment shown in FIG. 39, the rear edge 72' has a pear shape as viewed from a front perspective.

As seen in FIG. 39, the widest portion of the covering assembly 30' is preferably at the mouth height where the rear edge 72' extends preferably no more than 1½ inches past each lateral mouth edge. This distance may be alternatively one inch or less.

The wall structure 36e' has a pre-formed cup shape bounding a volume V within which the person's nose projects with the frame 32e' in the operative position on the person's head H and the wall structure 36e' in the blocking position.

The rear edge 72e' may by itself seal around the wearer's nose or may act in conjunction with the frame 32e' to effect a seal.

At least a portion of the rear edge 72e' moves up to, and preferably against, the person's frontal face region 220 as an incident of changing the wall structure 36e' from the staging position into the blocking position.

The same type of structure as described hereinabove may be used to apply at least a slight pressure of the rear edge 72e' against the wearer's frontal face region 220 in the blocking position. Within the generic showing of those structure herein, ratcheting arrangements, detent arrangements, cam arrangements, etc. might be utilized. Alternatively, or additionally, at least one component can be connected between the covering assembly 30 and at least one of the frame 32, a part of the person, and a structure on the person. As only examples, elongate components, with or without an elastic nature can be used. Over center biasing arrangements may cause the wall structure 36e' to be urged into each of the blocking and staging positions as each is approached.

It is desirable, but not required, that as an incident of the wall structure 36 moving from the staging position into the blocking position, the rear edge 72 is caused to be biased, or at least held, against the person's frontal face region 220, or maintained consistently in one or more blocking positions near, or against, the person's frontal face region. Alternatively, the biasing action may be induced by the subsequent manipulation of one or more components connected between the covering assembly and frame/person, or structure on the person with the wall structure 36 already in the blocking position.

As in all embodiments, the material defining the rear edge 72e', and/or the construction thereof, may allow conforming to the person's face contour under pressure.

In one form, as shown in FIG. 33, the wall structure 36e' may have a cup-shaped portion 240 of preferably flexible, but potentially more rigid, configuration that defines the volume V placed over the person's nose and mouth, and an outturned flange 242 defining the rear edge 72e'.

As shown in FIG. 33, an alternative subframe 244 may extend over part, or the entirety, of the generally circular shape of the rear edge 72e'. The subframe 244 may be bendable to be re-shaped to different configurations that will be maintained even when no force is applied. As an example, a bendable wire embedded in the flange 242 can be bent and will hold a bent shape. Thus, a person can re-shape the flange 242 to comfortably match the rear edge 72e' to his/her frontal face region 220. The wall portion 240 may be flexible so as to allow a certain degree of deformation while maintaining the cup shape.

In FIGS. 37 and 38, an exemplary component is shown at 246, corresponding to that described above, to connect between the covering assembly 30 and at least one of the frame, part of the person, and structure on the person to produce a bias force. In this embodiment, the component 246 is provided at the bottom of the covering assembly 30. The component 246 has a generally cup-shaped body 248 with an open rear perimeter portion 250. With the wall structure 36 moved downwardly into/towards its blocking position, the component 246 resides adjacent to the person's chin 218. Part or all of the body 248 is made of an elastic material so that while initially a volume at 252, bounded by the relaxed body 248, is substantially less than the volume of the person's chin 218, the body 248 can be stretched downwardly and around the chin 218. The stretched body 248 will have restoring forces that cause it to grip the person's chin 218 to maintain a frictional engagement.

A graspable tab 254 is connected to the body 248 to facilitate drawing of the body 248 conformingly over the person's chin 218.

Accordingly, the entire wall structure associated with the covering assembly 30 can be changed from the staging position into the blocking position by manipulating the tab 254 and drawing the same downwardly. In the same motion, the body 248 can be stretched over the person's chin 218 to effect frictional grasping of the chin region. At the same time, this produces potentially a slight biasing force of the associated rear edge on the covering apparatus 30 against the frontal face region 220 of the person.

Changing of the wall structure on the covering assembly 30 from the blocking position into the staging position can be effected by again grasping the tab 254 and drawing the same upwardly and outwardly.

Thus, one continuous movement can be effected to each of: a) change the wall structure from the blocking position into the staging position; and b) change the wall structure from the staging position into the blocking position. At the same time, the presence of the tab 254 allows convenient manipulation of the covering assembly 30 without requiring that the user touch any parts of the wall structure that may effect contamination thereof.

The same type of tab 254', as shown in FIGS. 32 and 33, can be used in all embodiments.

As an alternative holding arrangement, as shown in FIG. 32, the flange 242, upon being drawn against a person's face, may cause the person's chin to wedge between flange portions, which move away from each other, as indicated by the arrows A1, A2, whereupon restoring forces cause a frictional gripping of the chin.

As explained above, the wall structures 30 might be separated and replaced by wall structures that are cleaner, different in appearance, etc.

In FIG. 40, an alternative design is shown wherein the covering assembly 34" has a wall structure 36" with a cup-shaped wall 256 bounding a volume 258 and an out-turned, preferably formable, flange 260. A subframe 262 has a rim 264 which extends around an opening 266 to accept the wall 256 and has a surface 268 that is abuttable to an oppositely facing surface 270 on the wall structure 36" with the wall 256 moved in the direction of the arrow 272 into the opening 266.

This embodiment has a connector 274 associated with the rim 264 to mount the subframe 268 for pivoting movement about an axis 276 relative to an associated frame 32. This connection might be releasable to allow the subframe 268 to be changed. This releasable connection might allow a snap fitting of the subframe 268 so that it is releasably maintained in a predetermined position on the frame 32.

The wall structure 36" can be pressed through the opening 266 to place the surfaces 268, 270 in abutting relationship whereupon the flange surface 278, facing oppositely to the surface 270, performs the function of the rear edge 72 in the embodiments described above. Thus, with the connector 274 mounted to an appropriate frame, the subframe 268, together with the selected wall structure 36" making up the covering assembly 34", can be guidingly moved relative to an associated frame into the blocking position which bears the surface 278 against the person's frontal face region 220.

The subframe 262 may, in turn, have an associated subframe 280 performing as the aforementioned subframe 244 on the embodiment in FIG. 33. The flange 260 may also have a subframe 280' to facilitate independent shaping thereof.

Thus, the covering assembly 34" offers potentially the ability to shape the surface 278 as desired, with the ability to maintain virtually an unlimited number of different contours. At the same time, the wall structure 36" can be simply press fit into place and separated by reversing the assembly step to be replaced by another wall structure that may be either different in appearance, contain different information thereon, etc.

Thus, the invention offers the versatility of providing a generic frame with multiple interchangeable wall structures. While separate structures/connectors may be utilized to effect a more positive connection between the wall structure 36" and subframe 262, such as barbs, frictional engaging components, etc., a simple press fit, and frictionally maintained, connection is desirable from the standpoint of convenience. With the FIG. 40 structure, the press fit wall structure 36" is also captured against the wearer's face by the subframe 268.

Other press fit connections are described in other embodiments above.

It is anticipated that the inventive face covering apparatus can be widely used at particularly sporting events where fans are placed in tight quarters in tiered seating arrangements and food and drink are offered. Whereas in the past, conventional masks have been routinely carelessly applied, by covering potentially the nose and not the mouth, the mouth and not the nose, or neither the mouth nor the nose, the present invention affords a foolproof way of consistently placing the wall structure in the blocking position. Even if the wall structure is not moved relative to a respective frame, it can be comfortably placed in the blocking position and maintained therein by putting conventional frame structures on.

When a person desires to consume food or beverage, he/she can simply, potentially in one motion, change the wall structure from the blocking position into the staging position. After consumption, the reversal of this operation, potentially in a single motion, can be performed to cause the wall structure to consistently assume the blocking position.

As a further option, to reduce the likelihood that persons will not place the wall structure in the blocking position after food or beverage consumption, as shown in FIG. 41, an opening 282 can be provided through the wall structure 36 and fit with a resilient ring 284 to which a pivotable wall 286 is mounted. The ring 284 may be conventionally sealingly engaged in the opening 282, as depicted, and defines a through passage 288.

The wall 286 is spring biased to the solid line position wherein the passage 288 is blocked and can be moved to the dotted line position to open the passage 288.

By pressing a conduit/straw 290 in the direction of the arrow 292, the outer surface 294 of the conduit/straw 290 sealingly engages the surface 296 bounding the passage 288 and deflects the wall 286 from the solid line position into the dotted line position. This allows the conduit/straw to be utilized to draw a liquid, or the like, through the wall structure 36 without significantly compromising its blocking function.

In an alternative form, as shown in FIG. 42, a ring 284' is provided with deflectable flaps 298 which collectively sweep the conduit/straw 290 directed therethrough to allow the same penetration of the associated wall structure 36.

The foregoing disclosure of specific embodiments is intended to be illustrative of the broad concepts comprehended by the invention.

The invention claimed is:

1. A method for a person to control transmission of particles to and away from a frontal face region of the person, the method comprising steps of:
   obtaining a face covering apparatus comprising:
      a frame configured to be placed in an operative position on a person's head and releasably maintained in the operative position by at least one of: a) resting upon one or both ears of the person and b) frictionally engaging a part of the person's head; and
      a covering assembly on the frame and comprising a wall structure with: i) a first region configured to conform to a frontal face region of the person around a nose of the person; and ii) a second region configured to conform to the person's frontal face region around a mouth of the person,
      the face covering apparatus configured so that with the frame in the operative position on the person's head and the wall structure in a blocking position on the frame, the first and second regions on the wall structure together reside in a path of airborne particles moving:
         a) in a forward direction from nostrils and/or the mouth of the person; and b) in a rearward direction towards the person's nostrils and/or mouth, wherein the wall structure is movable relative to the frame between the blocking position and a staging position, wherein when the frame is in the operative position, at least a part of the wall structure is moved further away from the person's frontal face region in the staging position than when the wall structure is in the blocking position, wherein the wall structure moves angularly in relationship to the frame through at least 90° between the staging and blocking positions as viewed from a side perspective; and with the frame in the operative position on the person's head, moving the wall structure guidingly in a predetermined manner from the blocking position into the staging position wherein the wall structure does not reside directly forwardly of the person's frontal face region below a horizontal plane at or above a top of the person's mouth.

2. The method for controlling transmission of particles according to claim 1 wherein with the frame in the operative position on the person's head and the wall structure in the staging position, the wall structure does not reside directly forwardly of the person's frontal face region below a horizontal plane at or above eyes of the person.

3. The method for controlling transmission of particles according to claim 1 wherein with the frame in the operative position on the person's head and the wall structure in the staging position, the wall structure does not reside directly forwardly of the person's frontal face region and below a plane containing a top of the person's ears adjacent the person's head and a bridge of the person's nose.

4. The method for controlling transmission of particles according to claim 1 wherein with the frame in the operative position on the person's head the wall structure moves through an angular range of in excess of 90° between the blocking and staging positions.

5. The method for controlling transmission of particles according to claim 1 further comprising a step of moving the wall structure guidingly in a predetermined manner from the staging position back into the blocking position.

6. The method for controlling transmission of particles according to claim 5 wherein the wall structure has a pre-formed cup shape bounding a volume within which the nose of the person projects with the frame in the operative position on the person's head and the wall structure in the blocking position.

7. The method for controlling transmission of particles according to claim 6 wherein at least one of the covering assembly and the wall structure has a pear shape outline as viewed from a front perspective with the frame in the operative position on the person's head and the wall structure in the blocking position.

8. The method for controlling transmission of particles according to claim 6 wherein the wall structure has a rear edge extending around the volume and the step of moving the wall structure from the staging position back into the blocking position comprises causing the rear edge to move against the person's frontal face region.

9. The method for controlling transmission of particles according to claim 8 wherein the step of moving the wall structure from the staging position back into the blocking position comprises causing the rear edge to be biased against the person's frontal face region.

10. The method for controlling transmission of particles according to claim 9 wherein the rear edge has a formable shape and the rear edge is caused to re-shape and conform to a part of the person's frontal face region with the frame in the operative position on the person's head and the wall structure in the blocking position.

11. The method for controlling transmission of particles according to claim 8 wherein the rear edge has a pear shape as viewed from a front perspective with the frame in the operative position on the person's head and the wall structure in the blocking position and the person's mouth resides within the rear edge as viewed from a front perspective with the frame in the operative position on the person's head and the wall structure in the blocking position.

12. The method for controlling transmission of particles according to claim 8 wherein the rear edge is caused to be biased against the person's frontal face region as an incident of the wall structure moving from the staging position into the blocking position with the frame in the operative position on the person's head.

13. The method for controlling transmission of particles according to claim 8 wherein the rear edge is caused to be biased against the person's frontal face region as an incident of at least one component being connected between the covering assembly and at least one of: a) the frame; b) a part of the person; and c) a structure on the person.

14. The method for controlling transmission of particles according to claim 1 further comprising a step of introducing a component into at least one of the nostrils and mouth of the person with the frame in the operative position on the person's head and the wall structure in the staging position.

15. The method for controlling transmission of particles according to claim 1 wherein the wall structure resides fully above the person's eyes with the frame in the operative position on the person's head and the wall structure in the staging position.

16. The method for controlling transmission of particles according to claim 1 wherein the frame supports at least one lens residing in front of eyes of the person with the frame in the operative position on the person's head.

17. The method for controlling transmission of particles according to claim 1 wherein the step of placing the frame in the operative position comprises placing the frame in the operative position at an event and the step of obtaining a face covering apparatus comprises obtaining a face covering apparatus with information on the face covering apparatus relating to a product or service associated with the event and exposed and visible with the frame in the operative position on the person's head and the covering assembly in at least the blocking position, wherein the information is in the form of at least one of: a) at least one color; b) at least one word; and c) a logo.

18. The method for controlling transmission of particles according to claim 17 wherein the step of obtaining the face covering apparatus comprises obtaining the face covering apparatus through a vendor at the event.

19. The method for controlling transmission of particles according to claim 17 wherein the event is one of: a) a sporting event; b) a social event; and c) a business event.

20. The method for controlling transmission of particles according to claim 17 wherein the wall structure is a first wall structure and further comprising a step of removing the first wall structure from the frame and replacing the first wall structure with a second wall structure, wherein the first and second wall structures each has a front surface and the information on the first wall structure is on the front surface of the first wall structure, the second wall structure having information relating to a product or service associated with the event on the front surface of the second wall structure that is different than the information on the first wall structure.

21. The method for controlling transmission of particles according to claim 1 wherein the wall structure is a first wall structure and further comprising a step of removing the first wall structure from the frame and replacing the first wall structure with a second wall structure.

22. The method for controlling transmission of particles according to claim 21 wherein the step of replacing the first wall structure comprises connecting the second wall structure to a maintained position on the frame through a press fitting step.

23. The method for controlling transmission of particles according to claim 1 wherein the wall structure has a preformed cup shape with a rear edge and further comprising a step of re-shaping the covering assembly including at least the rear edge to a selected configuration and moving the wall structure from the blocking position into the staging position with the selected configuration maintained.

24. The method for controlling transmission of particles according to claim 1 wherein the covering assembly comprises a subframe with a rim that extends around an opening, wherein the wall structure has a cup-shaped wall that extends into the rim opening.

25. The method for controlling transmission of particles according to claim 24 wherein a discrete graspable tab is provided on the subframe rim, and further comprising a step of grasping the graspable tab and repositioning the graspable tab to change the wall structure between the blocking and staging positions.

26. The method for controlling transmission of particles according to claim 24 wherein the rim extends continuously around the rim opening.

27. The method for controlling transmission of particles according to claim 24 wherein the wall structure has a flange that abuts to the rim with the cup-shaped wall extended into the rim opening.

28. The method for controlling transmission of particles according to claim 27 further comprising the step of separating the wall structure from the rim and press fitting a different wall structure with a second cup-shaped wall into an operative position on the rim.

29. The method for controlling transmission of particles according to claim 28 wherein the second cup-shaped wall has a second flange and the step of press fitting the different wall structure comprises directing the second cup-shaped wall into the rim opening and bearing the second flange against the rim.

30. The method for controlling transmission of particles according to according to claim 24 further comprising a step of causing the cup-shaped wall to be releasably maintained in the rim opening as an incident of the cup-shaped wall being extended into the rim opening.

* * * * *